(12) United States Patent
Bai et al.

(10) Patent No.: US 11,311,263 B2
(45) Date of Patent: Apr. 26, 2022

(54) AUTOMATIC ON-THE-FLY POSITRON EMISSION TOMOGRAPHY (PET) SCAN PLANNING AND OPTIMIZATION

(71) Applicant: KONINKLIJKE PHILIPS N.V., Eindhoven (NL)

(72) Inventors: Chuanyong Bai, Solon, OH (US); Andriy Andreyev, Willoughby Hills, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 41 days.

(21) Appl. No.: 16/768,065

(22) PCT Filed: Nov. 26, 2018

(86) PCT No.: PCT/EP2018/082466
§ 371 (c)(1),
(2) Date: May 28, 2020

(87) PCT Pub. No.: WO2019/110336
PCT Pub. Date: Jun. 13, 2019

(65) Prior Publication Data
US 2020/0352537 A1 Nov. 12, 2020

Related U.S. Application Data

(60) Provisional application No. 62/594,116, filed on Dec. 4, 2017.

(51) Int. Cl.
*A61B 6/00* (2006.01)
*G01N 23/04* (2018.01)
(Continued)

(52) U.S. Cl.
CPC .......... *A61B 6/5235* (2013.01); *A61B 6/032* (2013.01); *A61B 6/037* (2013.01); *A61B 6/582* (2013.01); *G06T 11/003* (2013.01); *G16H 30/20* (2018.01)

(58) Field of Classification Search
CPC ........ G16H 30/20; G16H 50/30; A61B 6/032; A61B 6/037; A61B 6/5235; A61B 6/582;
(Continued)

(56) References Cited

U.S. PATENT DOCUMENTS 5,844,241 A    12/1998  Liu
8,891,726 B2 * 11/2014  Wieczorek ........... A61B 6/4447
                                               378/9
(Continued)

FOREIGN PATENT DOCUMENTS

CN    105976413 A    9/2016
WO    2014087311 A1  6/2014

OTHER PUBLICATIONS

International Search report and written opinion of PCT/EP2018/082466, dated Mar. 22, 2019.
(Continued)

*Primary Examiner* — Irakli Kiknadze

(57) ABSTRACT

A non-transitory computer-readable medium stores instructions executable by a processor to perform an acquisition and reconstruction method for a first image acquisition device. The method includes determining a scheduled acquisition time based on an attenuation map derived from imaging data from a second image acquisition device and a sensitivity matrix of the first image acquisition device; acquiring emission imaging data using the first image acquisition device, where the acquiring is scheduled to be performed over the scheduled acquisition time; during an initial portion of the acquiring, measuring a count or count rate of the acquired emission imaging data; adjusting the scheduled
(Continued)

acquisition time based on the measured count or count rate to generate an adjusted acquisition time while continuing the acquiring; stopping the acquiring at the adjusted acquisition time; and reconstructing the emission imaging data acquired over the adjusted acquisition time to generate one or more reconstructed images.

18 Claims, 4 Drawing Sheets

(51) Int. Cl.
*G16H 30/20* (2018.01)
*A61B 6/03* (2006.01)
*G06T 11/00* (2006.01)

(58) Field of Classification Search
CPC ....... A61B 6/507; A61B 6/5217; A61B 6/504; A61B 6/4417; A61B 6/503; A61B 6/5205; A61B 5/055; A61B 6/486; A61B 6/463; A61B 6/5264; A61B 6/583; A61B 6/481; A61B 6/508; A61B 6/06; A61B 6/469; A61B 6/501; A61B 6/545; A61B 5/0036; A61B 5/0042; A61B 5/0263; A61B 6/0487; A61B 10/0233; A61B 10/0266; A61B 18/12; A61B 18/20; A61B 2018/00577; A61B 2018/00595; A61B 2018/00904; A61B 2034/107; A61B 2034/2072; A61B 34/10; A61B 5/0095; A61B 6/027; A61B 6/5288; A61B 6/587; A61B 6/488; A61B 6/4057; A61B 6/4258; A61B 6/04; A61B 6/5258; A61B 6/4035; A61B 6/107; A61B 6/50; A61B 6/482; A61B 6/5247; A61B 6/4241; A61B 6/5282; A61B 6/4266; A61B 6/4028; A61B 6/4007; A61B 6/4014; A61B 6/4233; A61B 6/4447; G06T 11/003; G06T 11/006; G06T 5/50; G06T 5/001; G01J 1/46; G01T 1/1647; G01T 1/2914; G01T 1/2985; G01T 7/005; G01T 1/1615; G01T 1/1611; G01T 1/1648; G01T 1/1642; G01T 1/161; A61M 2205/18; A61M 2205/33; A61M 39/223; A61M 5/007; A61M 5/31535; G21G 1/0005; G21G 2001/0031; H01J 49/0004; H01J 49/0031; H01J 49/04; H05G 1/60; G06N 3/084; G06N 3/0454; G01N 23/046
USPC ...................................................... 378/19, 63
See application file for complete search history.

(56) References Cited

U.S. PATENT DOCUMENTS

| | | |
|---|---|---|
| 2006/0138315 A1 | 6/2006 | Williams |
| 2010/0030069 A1* | 2/2010 | Peter ....................... A61B 6/037 600/427 |
| 2010/0308817 A1 | 12/2010 | Vija |
| 2012/0056095 A1 | 3/2012 | Metzler |
| 2015/0036789 A1 | 2/2015 | Panin |
| 2016/0071263 A1* | 3/2016 | Thiruvenkadam ...... G06T 7/136 382/131 |
| 2016/0081635 A1* | 3/2016 | Divine ................... A61B 6/488 378/19 |
| 2017/0042492 A1* | 2/2017 | Noshi .................. A61B 6/4417 |
| 2017/0311919 A1* | 11/2017 | Gagnon ................. A61B 6/032 |
| 2019/0130569 A1* | 5/2019 | Liu ........................... G06T 5/50 |

OTHER PUBLICATIONS

Boellaard, R. et al "Standards for PET Image Acquisition and Quantitative Data Analysis", Journal of Nuclear Medicine, vol. 50, No. 5 (Suppl), 2009.

Zhang, J. et al "FDG Dose Reduction Potential of a Next Generation Digital Detector PET/CT System: Initial Clinical Demonstration in Wholebody Imaging", Journal Nuclear Medicine, vol. 56, Suppl. 31823, 2015.

Zhang, J. "Evaluation of Speed of PET Acquisition: How fase can we go?—A Validation of list Mode PET Simulation Approach with True Acquisitions", Journal Nuclear Medicine, vol. 58, Suppl. 1435, 2017.

Bach-Gansmo, T. et al. "Variation in urinary excretion of FDG, yet another uncertainty in quantitative PET", Acta Radiologica Short Reports, 2012.

* cited by examiner

AUTOMATIC ON-THE-FLY POSITRON EMISSION TOMOGRAPHY (PET) SCAN PLANNING AND OPTIMIZATION

CROSS-REFERENCE TO PRIOR APPLICATIONS

This application is the U.S. National Phase application under 35 U.S.C. § 371 of International Application No. PCT/EP2018/082466, filed on Nov. 26, 2018, which claims the benefit of U.S. Provisional Patent Application No. 62/594,116, filed on Dec. 4, 2017. These applications are hereby incorporated by reference herein.

FIELD

The following relates generally to the medical imaging arts, emission imaging arts, positron emission tomography (PET) imaging arts, single photon emission computed tomography (SPECT) imaging arts, and related arts.

BACKGROUND

Current clinical practice for planning positron emission tomography (PET) considers four factors: injected dose, patient size (e.g., body-mass-index, or BMI), uptake time (time between injection and PET scan), and scanning time per table position (or table traverse speed in continuous table motion acquisition). One common practice is that when the waiting time and scanning time per table position are set, the injected dose can be adjusted based on patient size (in general the larger is the patients weight or the BMI, the more dose is administered) to ensure image quality for accurate diagnosis. Another common practice is to adjust the scanning time per table position according to the injected dose (in general, the higher the dose, the shorter is the scanning time per table position). The primary purpose of such practice is to acquire sufficient counts for reliable image reconstruction and image quality for diagnosis.

In the above approach, the PET scan is only empirically optimized based on statistics from prior patient studies. It is not optimized for personalized imaging of the patient, i.e., for the specific patient and/or for the specific scan the patient is undergoing. Specifically, many variables (see, e.g., Boellaard R. Standards for PET image acquisition and quantitative data analysis. J Nucl Med 2009; 50 (Suppl. 1):11S-20S), such as dose calibration error, clock synchronization error, dose injection/residual dose measurement error, etc., can introduce uncertainties about the count level at the time the scan starts. Another factor is that patients have differences in fludeoxyglucose (FDG) urine clearance. Therefore, even with same dose/BMI/waiting time, the count level for a PET scan can vary. For short-life isotopes, a normal patient waiting time variation in a normal clinical workflow can introduce significant count level difference for PET scans. Since the scan time at each table position is set without the accurate knowledge of such variations, the PET acquisition is not adapted to such variations.

A common practice is to use a predetermined look-up-table when deciding the amount of injected dose based on patient BMI while assuming other conditions are the same. Such practice is not adaptive to the above mentioned variations. Also, an advanced image reconstruction that accurately models system performance can reliably predict the image quality at certain count level when the CT image is available. If a recent computed tomography (CT) image is available for a patient before the PET/CT scan, a physician can use a tool to determine the dose that needs to be injected so that he/she can confidently prescribe the minimal dose for the patient while having the assurance of sufficient image quality. For example, as described in Zhang J, et al. (FDG Dose Reduction Potential of a Next Generation Digital Detector PET/CT System: Initial Clinical Demonstration in Wholebody Imaging. *J Nucl Med* May 1, 2015 vol. 56 no. supplement 3 1823), multiple patient scans were performed following a standard clinical protocol. However, when using the data retrospectively to determine how much more dose reduction can be achieved, Zhang shows that FDG dose can be reduced by up to 70% without compromising diagnostic image quality and quantitation. Zhang J, et al. (Evaluation of speed of PET acquisition: How fast can we go?—A validation of list mode PET simulation approach with true acquisitions. *J Nucl Med* May 1, 2017 vol. 58 no. supplement 1 435) studies the impact of patient size (e.g., BMI) on scan time. These approaches are either retrospective or not adaptive to an individual patient and/or to the variation in a typical clinical workflow for patient scans.

The following discloses new and improved systems and methods to overcome these problems.

SUMMARY

In one disclosed aspect, a non-transitory computer-readable medium stores instructions readable and executable by a workstation including at least one electronic processor to perform an acquisition and reconstruction method. The method includes: acquiring emission imaging data using an emission image acquisition device wherein the acquiring is scheduled to be performed over an acquisition time; during the acquiring, measuring a count or count rate of the acquired emission imaging data; during the acquiring, adjusting the acquisition time based on the measured count or count rate to generate an adjusted acquisition time; stopping the acquiring at the adjusted acquisition time; and reconstructing the emission imaging data acquired over the adjusted acquisition time to generate one or more reconstructed images.

In another disclosed aspect, an imaging system includes a positron emission tomography (PET) device; and at least one electronic processor programmed to: control the emission image acquisition device to acquire emission imaging data using wherein the acquiring is scheduled to be performed over an acquisition time; during the acquiring, measuring a count or count rate of the acquired emission imaging data; during the acquiring, adjusting the acquisition time based on the measured count or count rate to generate an adjusted acquisition time; stopping the acquiring at the adjusted acquisition time; and reconstructing the emission imaging data acquired over the adjusted acquisition time to generate one or more reconstructed images.

In another disclosed aspect, an image acquisition and reconstruction method includes: adjusting an acquisition time based on a measured count rate of emission imaging data acquired over a scheduled dynamic acquisition time; and reconstructing one or more frames or positions of the emission imaging data acquired over adjusted acquisition time to generate one or more reconstructed images.

One advantage resides in using different image acquisition times at different table positions to achieve a uniform image quality.

Another advantage resides in improved image quality and/or reduced scan time by automatically adjusting an image acquisition time based on a measured count rate.

Another advantage resides in compensating for potential problems (e.g., dose mis-calibration, clock desynchronization, loner uptake time, urinary clearance, and so forth) with a measured count rate to compute an image acquisition time.

Another advantage resides in improved scheduling of parameters of the acquisition (e.g. acquisition time, radiopharmaceutical dosage).

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
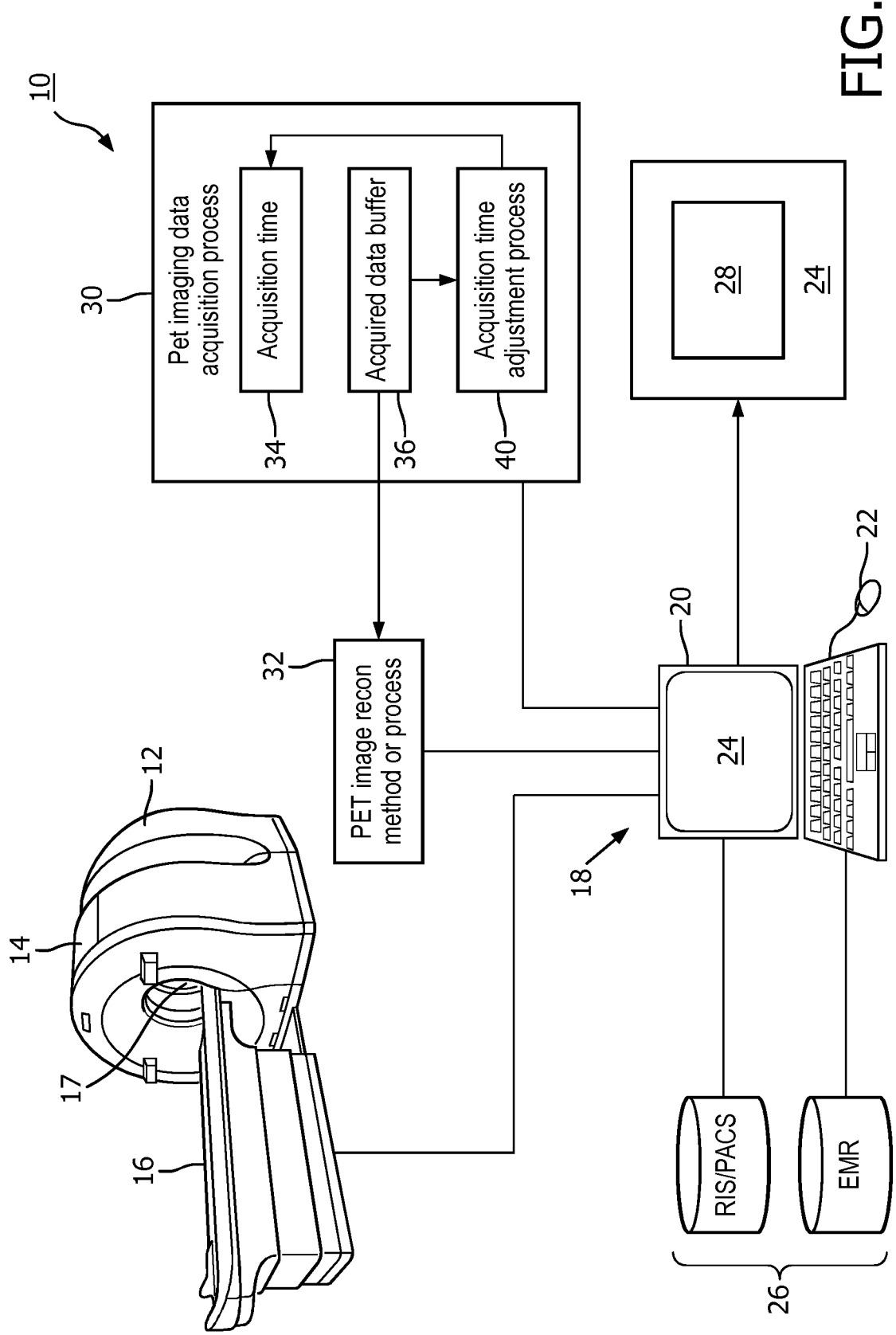
FIG. 1 diagrammatically shows image reconstruction system according to one aspect.

Existing CT/PET workflow entails administering the radiopharmaceutical for PET, followed by a defined time interval commonly on the order of an hour during which the patient is expected to remain at rest. The patient is then loaded into the CT/PET system, and CT imaging is performed to establish the axial FOV and to generate an attenuation map for use in PET reconstruction. The PET imaging data acquisition is then performed, either as a single acquisition interval or, for longer axial FOV, stepwise at multiple bed positions. In selecting the radiopharmaceutical dose and the acquisition time(s), medical personnel are guided by standard settings for the type of imaging session being performed and the wait period between administration of the radiopharmaceutical and commencement of imaging, with dose adjustment for patient body mass index (BMI). The dose and acquisition time settings are designed to ensure that sufficient positron-electron annihilation events are recorded to provide desired image quality as measured by a signal-to-noise-ratio (SNR) or other image quality metrics.

However, this approach has significant problems. There are numerous sources of potential error, such as dose calibration errors, timing errors, individual patient differences in anatomical morphology, urinary clearance of the radiopharmaceutical, and so forth. These can lead to the acquired counts being insufficient to achieve the desired level of image quality. A margin can be built into the dose to accommodate individual patient differences, but this may result in a higher than necessary radiopharmaceutical dose (and hence unnecessarily high radiation exposure to the patient and/or hospital workers). Likewise, a margin can be built into the acquisition time to accommodate individual patient differences, but this may result in a longer PET imaging session length than necessary.

In one disclosed embodiment, an "on the fly" adjustment of the PET imaging data acquisition time(s) is performed on the basis of the actually measured count rate. Advantageously, this does not require any added imaging operations—rather, the initial count rate is measured at or near the start of the clinical imaging data collection, and is used to adjust the acquisition time. In one approach, a calibration between initial count rate (e.g., for the first 30 sec) and acquisition time is generated empirically from historical PET imaging data, and is thereafter used to select the acquisition time. If the half-life of the radiopharmaceutical is sufficiently long so that the count rate can be expected to be constant over the acquisition time, then the acquisition time can be estimated as a target total counts estimated from or divided by the initial count rate. If the half-life is too short to neglect, then the acquisition time can be obtained by solving the following relation for the time t at which Counts(t) equals the target total counts:

$$\text{Counts}(t) = \int_0^t C_0 e^{-t/\tau} dt$$

where $C_o$ represents the measured initial count rate and $\tau$ represents the mean lifetime of the radiopharmaceutical. In more elaborate approaches, the attenuation map and a sensitivity matrix of the PET scanner is used to refine the acquisition time determination.

The acquisition time optimization can also optionally be spatially specific. In one approach, the count rates for angular bins spanning the 180° tomographic range are measured and the acquisition time is chosen to ensure that every angular bin has sufficient data. This can be useful to account for spatially varying count rates due to excessive patient attenuation in a certain angular direction. In another approach, a fast reconstruction of the initial imaging data is performed to generate a rough "image" of count rate per unit volume of the patient, and the acquisition time chosen to ensure sufficient count rate specifically for a spatial region of interest.

In the case of multi-bed position sessions, the acquisition time adjustment based on initial counts feedback for each bed position can assist in maintaining uniformity over the multiple bed positions. However, the disclosed approach is also readily employed for single-bed position acquisitions.

In another aspect, if a prior CT image of the patient is available, as for example might be the case for a follow-up PET imaging examination performed after one or more radiation therapy sessions, this may be used to more precisely tailor the dose for the specific patient. In this case an attenuation map can be generated from the prior CT image if the patient does not have significant weight loss from previous patient scans and/or radiation sessions, and is used along with a sensitivity matrix of the PET scanner to predict the counts and/or count rate. If a previous PET study of the patient is available, then the task of optimizing the acquisition is even more straightforward. Specifically, the dosage can then be adjusted to shift the predicted counts or count rate to a target value.

Advanced PET reconstruction algorithms can accurately model the performance the PET system, in terms of sensitivity, crystal/detector/gantry geometry, and so on. Radiopharmaceuticals have relatively defined update distribution in a patient body. Taking the advantage of these two pieces of prior knowledge, when the CT image of a patient is available, the reconstruction algorithm can be used to predict the level of counts required in order to achieve the expected image quality.

In some example embodiments, using the CT image, the portion of the CT image corresponding to the PET scan at the given table position is identified. The position of this portion of the CT image relative to the patient body can be approximated using approaches such as patient atlas, etc. In turn, the rough relative (not absolute or precise) pharmaceutical distribution can be modelled. Then using the system modelling approaches in the advanced reconstruction with the attenuation map converted from the CT image, one can predict the image quality as a function of expected acquired counts at the specific table position, depending on the patient's attenuation at that location. This provides a target total counts that can be used to select the acquisition time, and/or can be used in "on the fly" embodiments to provide a target total counts for adjusting the acquisition time based on the measured initial counts rate.

Although described herein for PET imaging systems, the disclosed approaches can be a hybrid PET/computed tomography (CT) imaging systems; a gamma camera single photon emission computed tomography (SPECT) imaging system with transmission scan capability, hybrid SPECT/CT imaging systems, hybrid PET magnetic resonance (MR) imaging systems, and the like.

With reference to FIG. 1, an illustrative medical imaging system 10 is shown. As shown in FIG. 1, the system 10 includes an emission image acquisition device 12. In one example, the image acquisition device 12 can comprise a PET imaging device. In other examples, the image acquisition device 12 can be any other suitable image acquisition device (e.g., SPECT, hybrid devices, and the like). In some embodiments, a second image acquisition device 14 of a different modality than the emission image acquisition device 12. For example, the emission image acquisition device 12 can be a PET imaging device, and the second image acquisition device 14 can be a CT imaging device. In the illustrative example, the emission image acquisition device 12 and the second imaging device 14 are thus combined as a hybrid PET/CT device. A patient table 16 is arranged to load a patient into an examination region 17, and more particularly can move a prone or supine patient axially either into the examination region of the PET scanner 12 for PET imaging, or into the examination region of the CT scanner 14 for CT imaging.

The system 10 also includes an imaging device controller, e.g. a computer or workstation or other electronic data processing device 18 with typical components, such as at least one electronic processor 20, at least one user input device (e.g., a mouse, a keyboard, a trackball, and/or the like) 22, and a display device 24. The imaging device controller 18 also includes or is in operative communication with one or more non-transitory storage media 26 (such as a magnetic disk, RAID, or other magnetic storage medium; a solid state drive, flash drive, electronically erasable read-only memory (EEROM) or other electronic memory; an optical disk or other optical storage; various combinations thereof; or so forth). The display device 24 is configured to display a graphical user interface (GUI) 28.

The one or more non-transitory storage media 26 stores instructions which are readable and executable by the at least one electronic processor 20 to perform disclosed operations including performing a PET imaging data acquisition process 30 which controls the PET imaging acquisition device 12 to acquire imaging data, and a PET image reconstruction method or process 32 which processes the acquired PET imaging data to generate a reconstructed PET image. The PET imaging data acquisition process 30 performs image acquisition for a bed position. This acquisition is scheduled to be performed over an acquisition time 34. The PET imaging data are stored in an acquired data buffer 36 (e.g., stored on a non-transitory storage medium such as previously described). The stored PET imaging data may comprise list mode data in which 511 keV gamma ray detection events are stored with detection timestamps. Alternatively the stored PET imaging data may comprise coincident 511 keV gamma ray detection event pairs, where two 511 keV detection events are determined to be coincident if both occur within a defined coincidence time window. If list mode data are stored then a "count" suitably corresponds to a single 511 keV detection event; and moreover, coincidence processing of the list mode data is performed in downstream processing. If coincident 511 keV detection event pairs are stored then a "count" suitably corresponds to a 511 keV detection event pair.

The scheduled acquisition time 34 may be chosen based on various factors, such as the patient BMI, the radiopharmaceutical dose, the wait time between dose administration and commencement of the PET imaging data acquisition, or so forth, in order to ensure that a sufficient (target) total counts is obtained to reconstruct a PET image with a desired image quality. The radiopharmaceutical dose is chosen as a minimum dose expected to be sufficient to provide the target total counts over the scheduled acquisition time. Minimum dose is a clinical objective in order to minimize radiation exposure of the patient.

As previously discussed, however, numerous patient-specific or even imaging session-specific factors may result in the count rate (single or coincident pairs, depending upon the embodiment) differing significantly from that assumed when scheduling the acquisition time 34. Such factors may include, by way of non-limiting example: variation in radiopharmaceutical activity; differences in urinary clearance of the radiopharmaceutical; changes in BMI between the scheduling of the imaging session and the imaging data acquisition; metabolic differences amongst patients; and/or so forth. To account for this, an acquisition time adjustment process 40 (e.g., a subroutine or sub-process of the PET imaging data acquisition process 30) leverages the count rate initially observed in the clinical PET data stored in the PET imaging data buffer 36 to dynamically adjust the acquisition time 34. For example, if the initially scheduled acquisition time was chosen under an assumption of a certain count rate, then if the actual count rate observed for data collected in the buffer 36 is lower than this assumed count rate then the acquisition time 34 is increased to ensure sufficient total counts are detected. Conversely, if the actual count rate observed for data collected in the buffer 36 is higher than this assumed count rate then the acquisition time 34 may be decreased to provide for a faster imaging session without unacceptable loss in image quality. The PET imaging data acquisition process 30 stops the imaging data acquisition at the adjusted acquisition time.

In the case of multi-station PET imaging, the patient is imaged at two or more successive bed positions in order to scan an axial volume larger than the axial field of view (FOV) of the PET scanner 12. In this case, there will be a scheduled acquisition time 34 for each bed position, and the acquisition time adjustment process 40 is performed for each bed position using the initially acquired count rate to adjust the acquisition time 34 for that bed position to dynamically adjust the scheduled acquisition time. Advantageously, this can ensure that each bed position acquires the same target total counts (or, alternatively, may ensure that more counts are acquired for the bed position(s) at which a critical organ is imaged).

In cases where the acquisition time adjustment process 40 results in increasing the acquisition time to a longer time than the initially scheduled acquisition time, there may be some upper time limit imposed, i.e. the acquisition time adjustment process 40 is constrained to increase the acquisition time 34 to no higher than some upper limit time. This ensures that the imaging session is not extended by an unacceptably long time, so that for example the radiology laboratory can maintain a patient schedule.

The acquisition time adjustment process 40 leverages the count rate observed during an initial portion of the acquisition. For example, if the scheduled acquisition time is 5 minutes, the initial count rate may be the average count rate over the first 1-10 seconds of this scheduled 5 min acquisition time. If, for example, the measured initial count rate is lower than expected, then the acquisition time may be adjusted upward, e.g. to 6 min by way of non-limiting illustrative example. Conversely, if the measured initial count rate is higher than expected, then the acquisition time may be adjusted downward, e.g. to 4 min by way of non-limiting illustrative example. In other examples, the PET scanner 12 is configured to obtain a surview image of the patient through an entire scanning volume (e.g., 1 second per bed position) to determine a count rate for each bed position beforehand. Typically 10 million counts during 90 seconds acquisition per frame can be expected, resulting in a count rate of 100,000 counts per second which should be sufficient to determine the expected count rate with minimum noise fluctuations <1% and good margins. In one example, the time acquisition time can be set equal to T so that $\sqrt{C(T)}/C(T)<0.05$, where $C(T)$ is equal to detected counts during time period T, resulting in a 5% expected count noise variation.

The acquisition time adjustment process 40 leverages the count rate observed during an initial portion of the acquisition. This count rate may be the singles count rate in some embodiments, that is, the count rate of 511 keV detection events. Alternatively, this count rate may be the coincidences count rate in some embodiments, that is, the count rate of coincident 511 keV detection event pairs. (In the case of SPECT imaging, single photon events form the clinical data as there is no analog in SPECT to the coincident pairs in PET; hence the count rate for SPECT is the singles count rate).

Advantageously, the acquisition time adjustment process 40 leverages the count rate observed during an initial portion of the actual clinical PET imaging data acquisition. As this initial portion forms part of the overall clinical PET imaging data set, there is no additional data collected to perform the acquisition time adjustment. Moreover, as a typical PET data acquisition time is on the order of seconds to minutes or longer, whereas the processing required for an electronic processor (e.g. microprocessor) to calculate the acquisition time adjustment is typically on the order of milliseconds or faster, the operation of the acquisition time adjustment process 40 does not impose any delays on the imaging session.

With continuing reference to FIG. 1, the clinical PET imaging data stored in the PET imaging data buffer 36 (an initial portion of which was used by the acquisition time adjustment process 40 to calculate the acquisition time adjustment) is processed by the PET image reconstruction process 32 to generate a reconstructed PET image. The PET image reconstruction process 32 may employ any suitable image reconstruction process comporting with the coincident 511 keV pairs data, e.g. may employ filtered backprojection or some iterative image reconstruction process such as maximum likelihood expectation maximization (MLEM) or ordered subsets expectation maximization (OSEM), optionally further incorporating an edge-preserving prior or regularization, various image filtering, and/or so forth. The resulting reconstructed image may be displayed on the display 24 or otherwise utilized.

Figure 2:
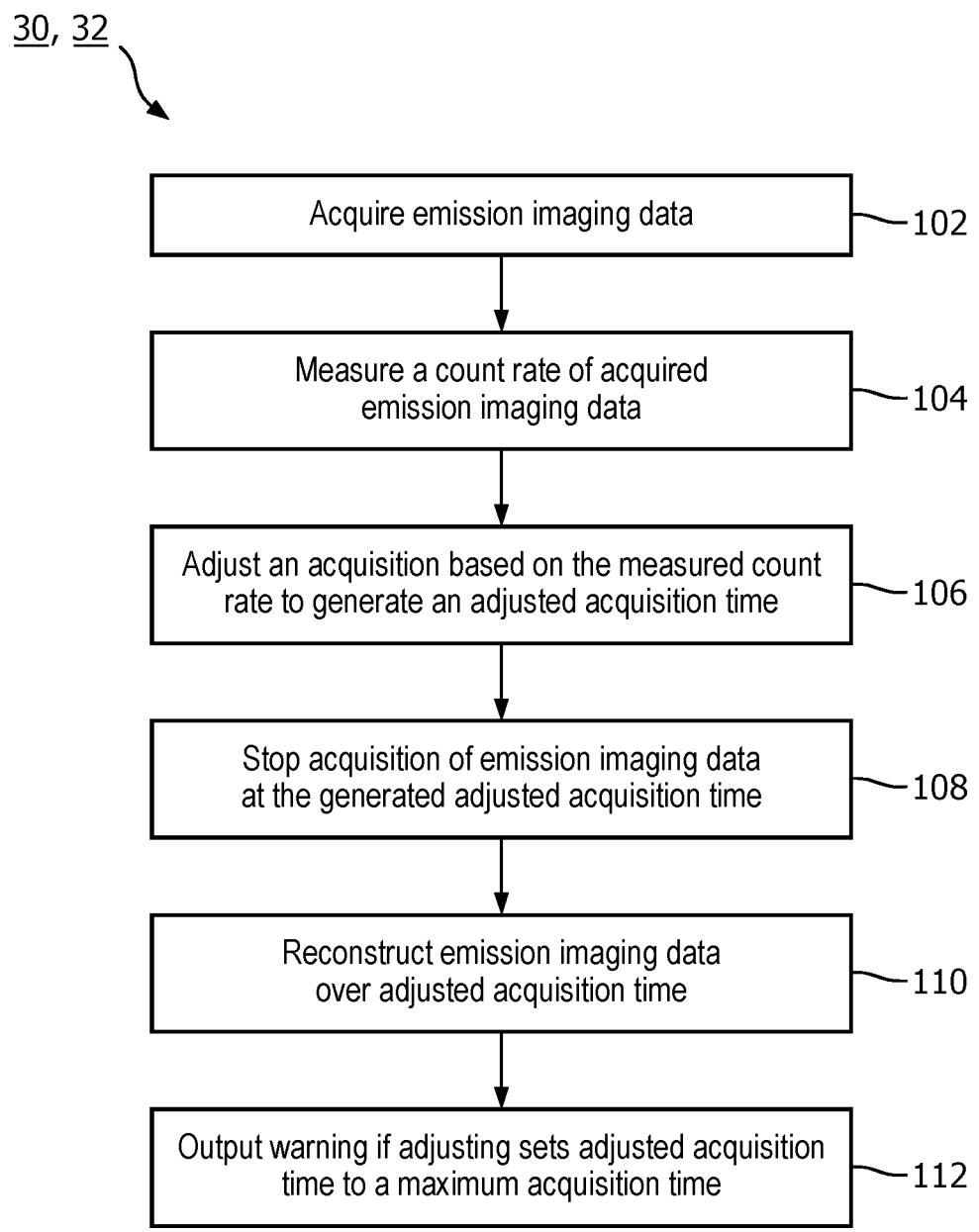
FIG. 2 shows an exemplary flow chart operation of the system of FIG. 1.

With reference to FIG. 2, an illustrative embodiment of the image acquisition and reconstruction processes 30, 32 is diagrammatically shown as a flowchart. At 102, the at least one electronic processor 20 is programmed to control the emission image acquisition device 12 to acquire emission imaging data. The acquiring of the emission imaging data is schedule to be performed over the acquisition time 34 (see FIG. 1).

At 104, during the acquiring of the emission imaging data, the at least one electronic processor 20 is programmed to execute the acquisition time adjustment process 40 to measure a count or a count rate of the acquired emission imaging data during an initial period of the data acquisition (e.g., the first 1-10 seconds may be sufficient if the scheduled acquisition time is on the order of minutes). At 106, also during the acquiring of the emission imaging data, the at least one electronic processor 20 is programmed to execute the acquisition time adjustment process 40 to dynamically adjust the acquisition time based on the measured count or count rate to generate an adjusted value of the acquisition time 34. In one example, the at least one electronic processor 20 is programmed to measure the count rate over a measurement time interval, and set the adjusted acquisition time to the lesser of (i) a target total counts estimated from or divided by the count rate or (ii) a maximum acquisition time. In another example, suitable for PET imaging with short half-life radioisotopes, the at least one electronic processor 20 is programmed to set the adjusted acquisition time to the time at which the time integral of the counts given by Counts(t) $=\int_o^t C_o e^{-t/\tau}\, dt$ reaches the target total counts. In a further example, the at least one electronic processor 20 is programmed to generate a calibration value between the count rate and the acquisition time using historical imaging data stored in the database 26. The at least one electronic processor 20 is programmed to use the generated calibration value to adjust the acquisition time to generate the adjusted acquisition time.

In the previous embodiments, the initial count rate is extrapolated to estimate when the total counts will reach a target total counts. In another example, the at least one electronic processor 20 is programmed to measure the count as a function of time over the acquiring, and set the adjusted acquisition time to the lesser of (i) a time at which the count reaches a target total counts or (ii) a maximum acquisition time. In this embodiment the effect is to stop the acquisition when the total counts reaches the target total counts, or when the "timeout" maximum acquisition time is reached (whichever is shorter).

In other embodiments, the at least one electronic processor 20 is programmed to measure count rates for angular bins spanning 180° of a tomographic range. The at least one electronic processor 20 is then programmed to adjust the acquisition time such that each angular bins includes an amount of data above a preselected data threshold. In some examples, the at least one electronic processor 20 is programmed to calculate the threshold for each bin as a product of the threshold amount of imaging data (e.g., an empirically optimized minimum number of counts) for the bin divided by or estimated from the count rate measured for the bin.

In further embodiments, the at least one electronic processor 20 is programmed to, during the acquiring of the emission imaging data, reconstruct an initially acquired portion of the emission imaging data to generate an initial image and determining a count or count rate per unit volume for the initial image. The at least one electronic processor 20 is then programmed to adjust the acquisition time to achieve a minimum count rate per unit volume over the initial image.

With continuing reference to FIG. 2, at 108, the at least one electronic processor 20 is programmed to stop the acquiring of the emission imaging data at the adjusted acquisition time.

At 110, the at least one electronic processor 20 is programmed to execute the PET image reconstruction process 32 (see FIG. 1) to reconstruct the emission imaging data acquired over the adjusted acquisition time to generate one or more reconstructed images. The reconstructed images can be, for example, displayed on the display device 24, or stored in the database 26.

At 112, the at least one electronic processor 20 is programmed to output a user-perceptible low counts warning if the adjusting sets the adjusted acquisition time to the maximum acquisition time while still not being able to satisfy minimum recommended counts requirement. The warning can be, for example, displayed on the display device 24, or output as an audio alarm on a loudspeaker (not shown).

The foregoing examples relate to "on the fly" embodiments in which count rates (or total counts) measured during the image acquisition are used to adjust the acquisition time 34. In other embodiments (which may optionally be combined with the on-the-fly aspect), the initially scheduled acquisition time 34 is set on a per-patient basis leveraging patient-specific information. In some such embodiments, prior to start of the acquiring of emission imaging data (e.g., from the PET scanner 12), the at least one electronic processor 20 is programmed to control the second image acquisition device (e.g., the CT scanner 14) to acquire second imaging data. The at least one electronic processor 20 is programmed to generate an attenuation map from the second imaging data. The at least one electronic processor 20 is then programmed to schedule the acquisition time for the acquiring using at least the generated attenuation map and a sensitivity matrix of the emission image acquisition device 12. In this embodiment, the at least one electronic processor 20 is programmed to adjust the acquisition time based on the measured count rate, the generated attenuation map, and the sensitivity matrix of the emission image acquisition device 12 to generate the adjusted acquisition time. In addition, the at least one electronic processor 20 is programmed to schedule a radiopharmaceutical dosage administered to a patient to be imaged by the emission image acquisition device 12 using at least the generated attenuation map and the sensitivity matrix of the emission image acquisition device.

Figure 3:
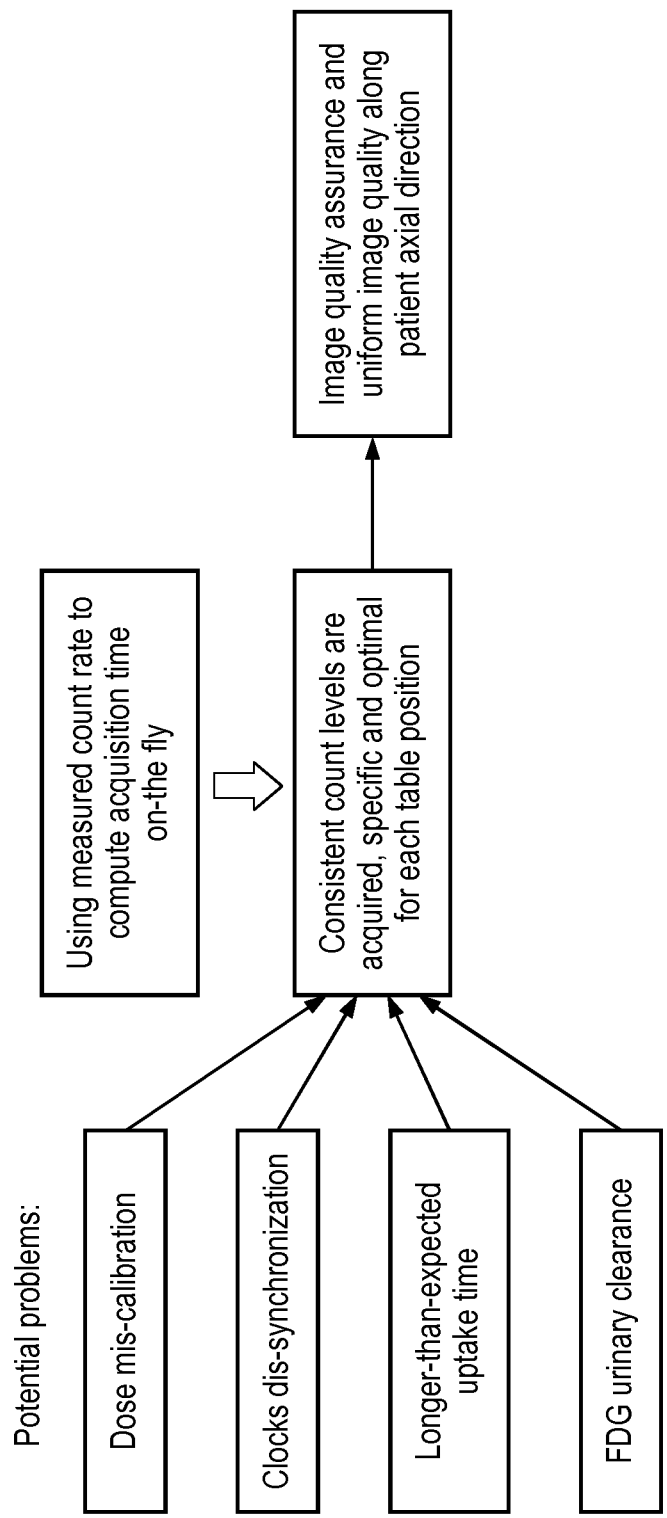
FIG. 3 illustratively shows an example operation of the system of FIG. 1.

FIG. 3 diagrammatically shows another representation of on-the-fly acquisition time adjustment. As shown in FIG. 3, potential problems, including radiopharmaceutical dose mis-calibration; desynchronization between clocks of the emission image acquisition device 12, a loner than expected uptake time, and FDG urinary clearance, can affect the image quality of the reconstructed images. Using the adjusted acquisition time, the emission image acquisition device 12 can acquire imaging data at consistence count levels in each table position to assurance a high image quality.

EXAMPLE

The following example relates to a whole-body FDG PET/CT study. In advanced PET image reconstruction with CT-based attenuation correction, system performance, such as sensitivity, uniformity, geometry, dead time, time-of-flight, and etc., can be accurately modeled. When the CT image of a patient is available, the FDG distribution of the body can be approximated. This can be performed with an FDG distribution atlas from a known database or a database generated from a large number of representing patient studies. Using this estimated FDG distribution, the attenuation map generated from the CT image, and the system model, the general image quality can be predicted when certain amount of counts are acquired. In this process, the estimated FDG distribution is not absolutely required, but can help to identify the region in which the image quality is more critical, such as mediastinum, liver, etc.

A specific PET/CT system can be developed to perform the above-described estimation of predicted image quality and acquired counts when a CT image of the patient is available. The relationship can be established by analyzing many patient studies with known size, count levels, etc. Alternatively, the relationship can be established for the individual patient using a fast imaging model or Monte Carlo simulation work using the CT image/attenuation map, the system performance model used in advanced image reconstruction. An estimated FDG distribution can be used to improve the model or simulation for the specific patient.

Figure 4:
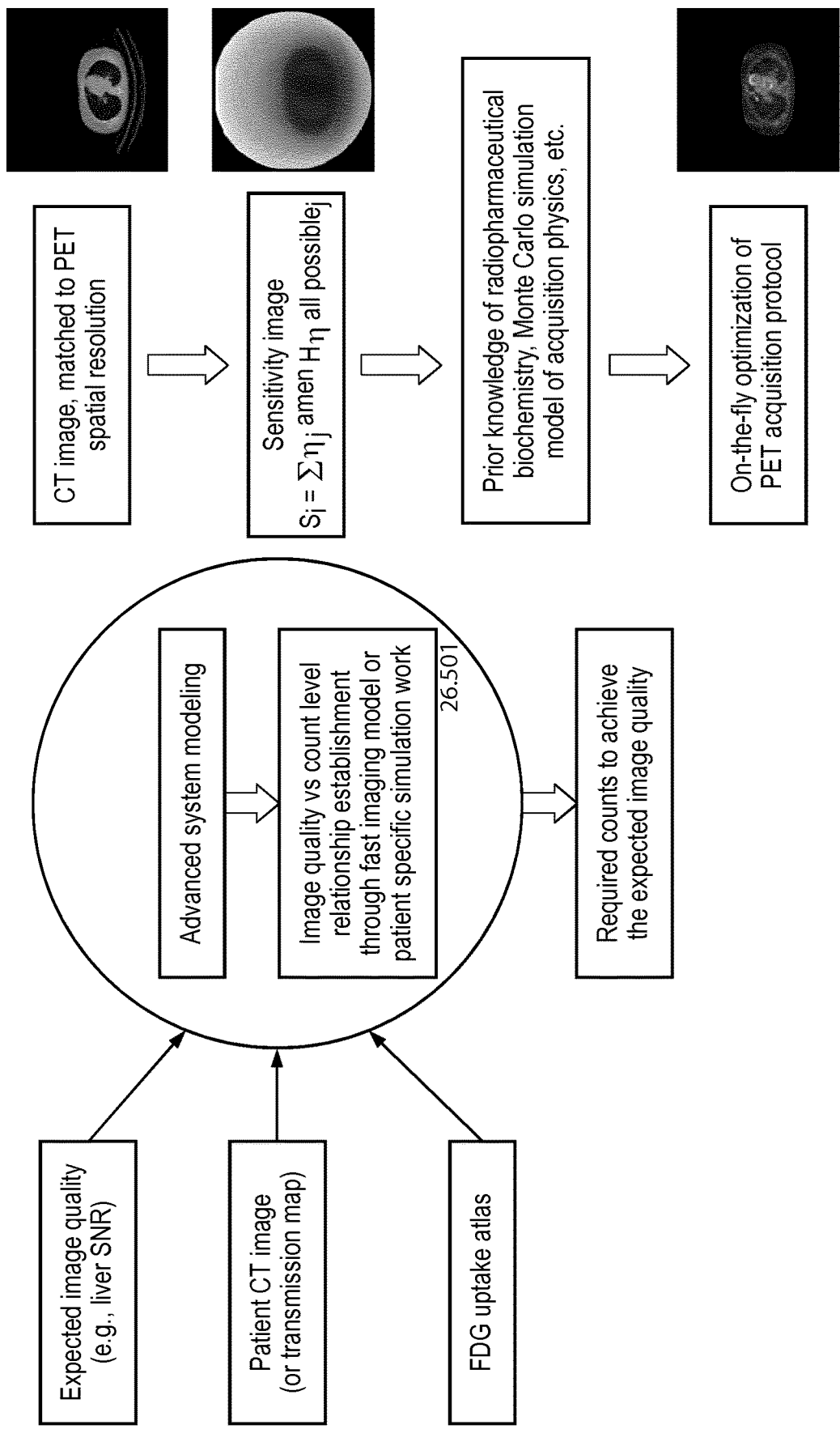
FIG. 4 illustratively shows another flow chart of the system of FIG. 1.

FIG. 4 illustrates how the disclosed PET/CT system receives inputs from the physician of specified image quality expectation, the patient CT image, and generates the output of required counts to achieve the expected image quality. As shown in FIG. 4, an expected image quality, a patient CT image, and/or an FDG uptake atlas are used as inputs. The image quality vs count level relationship can be established through imaging model or simulation work and saved for the tool for the particular system, or can be established for each specific patient on-the-fly.

When the disclosed system is used for automatic and on-the-fly PET planning and optimization, at each table position of the PET scan, the system measures the true count rate at the table position. The system takes the input of expected image quality, the predicted counts needed to achieve such image quality, and the measured count rate, to calculate/optimize the acquisition time for the specific table position.

For the application of patient dose reduction and minimization, if a recent CT of the patient is available (and there is no significant BMI change of the patient), then the system can estimate the radiotracer distribution in the patient and the count rate at a representative table position for the planned PET scan (such as the table position covering liver) prior to radiopharmaceutical injection. Also when short-liver radiotracers are used (e.g., Rb-82), the CT scan is typically done before the injection of such radiotracer. Using the planned PET acquisition time, the system can then calculate the optimal dose that is needed and recommend the optimal dose to the physicians. Physicians can then prescribe the injected dose to the patient, with the confidence that the dose is minimal but the image quality is assured based on the imaging study (i.e., small lesion detection). In the later on PET acquisition, the automatic and on-the-fly planning application of this invention is also used to double assure the desired counts are acquired at each table position, in turn, the desired image quality is achieved.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium storing instructions that, when executed by at least one processor, cause the at least one processor to perform an acquisition and reconstruction method using a first image acquisition device, comprising:
    acquiring imaging data using a second image acquisition device of a different modality than the first image acquisition device;
    determining a scheduled acquisition time based on at least an attenuation map derived from the imaging data and a sensitivity matrix of the first image acquisition device;
    subsequently acquiring emission imaging data using the first image acquisition device, wherein the acquiring is initially scheduled to be performed over the scheduled acquisition time;
    during an initial portion of the acquiring, measuring a count or count rate of the acquired emission imaging data;
    adjusting the scheduled acquisition time based on the measured count or count rate to generate an adjusted acquisition time while continuing to acquire the emission imaging data;
    stopping the acquiring at the adjusted acquisition time; and
    reconstructing the emission imaging data acquired over the adjusted acquisition time to generate one or more reconstructed images.

2. The non-transitory computer-readable medium of claim 1, wherein the measuring comprises measuring the count rate over a measurement time interval, and wherein the adjusting comprises setting the adjusted acquisition time to a lesser of (i) a time to acquire a target total counts estimated from the count rate or (ii) a predetermined maximum acquisition time.

3. The non-transitory computer-readable medium of claim 1, wherein the measuring comprises measuring the count as a function of time over the initial portion of the acquiring, and the adjusting comprises setting the adjusted acquisition time to a lesser of (i) a time at which the count reaches a target total counts or (ii) a predetermined maximum acquisition time.

4. The non-transitory computer-readable medium of claim 1, wherein the method further comprises:
    outputting a user-perceptible low counts warning the adjusting sets the adjusted acquisition time to a predetermined maximum acquisition time.

5. The non-transitory computer-readable medium of claim 1, wherein the method further comprises:
    generating a calibration value between the count rate and the scheduled acquisition time using historical imaging data stored in a database; and
    using the generated calibration value to adjust the scheduled acquisition time to generate the adjusted acquisition time.

6. The non-transitory computer-readable medium of claim 1, wherein the first image acquisition device is a positron emission tomography (PET) imaging device and the second image acquisition device is a computed tomography (CT) imaging device.

7. The non-transitory computer-readable medium of claim 1, wherein the adjusting comprises adjusting the scheduled acquisition time based on the measured count rate, the generated attenuation map, and the sensitivity matrix of the first image acquisition device to generate the adjusted acquisition time.

8. The non-transitory computer-readable medium of claim 1, wherein the method further comprises:
    scheduling a radiopharmaceutical dosage administered to a patient to be imaged by the first image acquisition device using at least the generated attenuation map and the sensitivity matrix of the first image acquisition device.

9. The non-transitory computer-readable medium of claim 1, wherein:
    the measuring includes measuring count rates for angular bins spanning 180° of a tomographic range; and
    the adjusting includes adjusting the scheduled acquisition time such that each of the angular bins includes an amount of data above a preselected data threshold.

10. The non-transitory computer-readable medium of claim 1, wherein:
    the measuring includes, during the initial portion of the acquiring, reconstructing an initially acquired portion of the emission imaging data to generate an initial image and determining the count or count rate per unit volume for the initial image; and
    the adjusting includes adjusting the scheduled acquisition time to achieve a minimum counts per unit volume over the initial image.

11. An imaging system, comprising:
    a positron emission tomography (PET) device;
    a computed tomography (CT) device;
    at least one processor; and
    a non-transitory memory storing instructions that, when executed by the at least one processor, cause the at least one processor to:
    control the CT device to acquire CT imaging data;
    determine a scheduled acquisition time based on at least an attenuation map derived from the CT imaging data and a sensitivity matrix of the PET device;
    control the PET device to acquire emission imaging data, wherein the acquiring is scheduled to be performed over the scheduled acquisition time;
    during an initial portion of the acquiring, measure a count or count rate of the acquired emission imaging data;
    adjust the scheduled acquisition time based on the measured count or count rate to generate an adjusted acquisition time while continuing to control the PET device to acquire the emission imaging data;
    control the PET device to stop the acquiring at the adjusted acquisition time; and
    reconstruct the emission imaging data acquired over the adjusted acquisition time to generate one or more reconstructed images.

12. The imaging system of claim 11, wherein the instructions further cause the at least one processor to:
    measure the count rate over a measurement time interval; and
    set the adjusted acquisition time to a lesser of (i) a target total counts estimated from the count rate or (ii) a predetermined maximum acquisition time.

13. The imaging system of claim 11, wherein the instructions further cause the at least one processor to:
    measure the count as a function of time over the initial portion of the acquiring; and
    set the adjusted acquisition time to a lesser of (i) a time at which the count reaches a target total counts or (ii) a predetermined maximum acquisition time.

14. The imaging system of claim 11, wherein the instructions further cause the at least one processor to:
control a display device to display a user-perceptible low counts warning when the adjusting sets the adjusted acquisition time to a predetermined maximum acquisition time.

15. The imaging system of claim 11, wherein the instructions further cause the at least one processor to:
generate a calibration value between the count rate and the scheduled acquisition time using historical imaging data stored in a database; and
use the generated calibration value to adjust the scheduled acquisition time to generate the adjusted acquisition time.

16. The imaging system of claim 11, wherein the instructions further cause the at least one processor to:
adjust the acquisition time based on the measured count rate, the generated attenuation map, and the sensitivity matrix of the PET device to generate the adjusted acquisition time.

17. A method of acquiring and reconstructing emission images of a patient using a first image acquisition device, the method comprising:
acquiring imaging data from a second image acquisition device of a different modality than the first image acquisition device;
determining a scheduled acquisition time based on at least an attenuation map derived from the imaging data and a sensitivity matrix of the first image acquisition device;
acquiring emission imaging data from the first image acquisition device, wherein the acquiring is scheduled to be performed over the scheduled acquisition time;
during an initial portion of the acquiring, measuring a count rate of the emission imaging data;
adjusting the scheduled acquisition time based on the measured count rate of the emission imaging data to provide an adjusted acquisition time while continuing to acquire the emission imaging data; and
reconstructing one or more frames or positions of the emission imaging data acquired over adjusted acquisition time to generate one or more reconstructed images.

18. The method of claim 17, further comprising:
displaying a user-perceptible low counts warning when the adjusting provides the adjusted acquisition time to a maximum acquisition time.

* * * * *